United States Patent
Vija et al.

(10) Patent No.: US 11,948,290 B2
(45) Date of Patent: Apr. 2, 2024

(54) INDIVIDUAL CHANNEL CHARACTERIZATION OF COLLIMATOR

(71) Applicant: Siemens Medical Solutions USA, Inc., Malvern, PA (US)

(72) Inventors: Alexander Hans Vija, Evanston, IL (US); Francesc dAssis Massanes Basi, Chicago, IL (US); Amos Yahill, Stony Brook, NY (US); Ronald E. Malmin, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 875 days.

(21) Appl. No.: 16/590,657

(22) Filed: Oct. 2, 2019

(65) Prior Publication Data

US 2021/0103158 A1 Apr. 8, 2021

(51) Int. Cl.
| | | |
|---|---|---|
| *G02B 27/30* | (2006.01) | |
| *A61B 6/03* | (2006.01) | |
| *G01M 11/02* | (2006.01) | |
| *G01M 11/08* | (2006.01) | |
| *G06T 7/00* | (2017.01) | |
| *G21K 1/02* | (2006.01) | |
| *A61B 6/58* | (2024.01) | |

(52) U.S. Cl.
CPC ....... *G06T 7/0006* (2013.01); *G01M 11/0207* (2013.01); *G01M 11/081* (2013.01); *G02B 27/30* (2013.01); *G21K 1/02* (2013.01); *A61B 6/037* (2013.01); *A61B 6/583* (2013.01); *G06T 2207/30164* (2013.01)

(58) Field of Classification Search
USPC ........................................................ 382/147
See application file for complete search history.

(56) References Cited

U.S. PATENT DOCUMENTS

| | | | |
|---|---|---|---|
| 3,943,366 A | 3/1976 | Platz et al. | |
| 8,340,386 B2 | 12/2012 | Malmin | |
| 8,483,460 B2 | 7/2013 | Malmin | |
| 9,622,714 B2 * | 4/2017 | Hawman | A61B 6/037 |
| 2007/0217672 A1 * | 9/2007 | Shannon | G06F 18/00 |
| | | | 382/152 |
| 2020/0160497 A1 * | 5/2020 | Shah | G06T 7/001 |

OTHER PUBLICATIONS

Malmin, et al., "Collimator Angulation Error and Its Effect on SPECT." Journal of Nuclear Medicine 31(5): 655-659.

* cited by examiner

*Primary Examiner* — Mikhail Itskovich (57) ABSTRACT

A framework for characterization of a collimator. In accordance with one aspect, first and second sides of the collimator are photographed to generate first and second image data. An optical characterization map (OCM) may be generated based on the first and second image data, wherein the optical characterization map characterizes the individual channels of the collimator. Quality assessment or image reconstruction may then be performed based on the OCM.

20 Claims, 7 Drawing Sheets

INDIVIDUAL CHANNEL CHARACTERIZATION OF COLLIMATOR

TECHNICAL FIELD

The present disclosure generally relates to nuclear imaging, and more particularly to characterizing individual channels of collimators for nuclear imaging.

BACKGROUND

Collimators are frequently used for radiation image formation. A collimator is a physical device that allows only photons passing along a direct path from the radiation source to strike the photon detector, thereby minimizing detection of beams of scattered or secondary radiation. A collimator has collimating apertures (referred herein as "channels") and is positioned between the photon detector and the subject to screen out all of the photons except those directed along a straight line through the collimator channels between a particular part of the subject and a corresponding particular part of the detector. The collimator is made of a radiation opaque material such as lead, and collimating channels have been formed therein by various means such as drilling, casting or lamination of corrugated strips of lead foil.

Without loss of generality, consider as an example the image formation for Single Photon Emission Computed Tomography (SPECT) images, whereby the image formation typically occurs with a parallel-hole-collimator (PHC), such as a low energy high-resolution (LEHR) collimator. A subject (patient) is infused with a radioactive substance that emits gamma rays. The photon detector measures energy and location of the impinging photons after they passed or interacted with the collimator. If the detector is struck by undesired photons, such as those passing along non-direct paths to the gamma camera transducer, performance of the imaging system can be compromised.

Collimators are typically manufactured using, for example, casting, stacking corrugated foils, extruding, three-dimensional (3D) printing, etc. Cast collimators are usually made with pins suspended in a mold of molten lead. Foiled collimators are typically built by stacking corrugated foils, such as a stack of half hex foils for hexagonal holes. 3D printed collimators are typically produced by either an additive (i.e., adding layers of material) or a subtractive method (i.e., removing layers of material).

A collimator is usually manufactured with some tolerances, depending on the specific task. A collimator has a characteristic design of a pattern of channels with specific properties, such as hole location, cross section and direction that is defined by, e.g., normal vector of the cross section. Based on the type of collimator manufacturing, specific collimator characteristics may be of importance. For instance, a cast collimator maintains its hole shape very well but its hole direction may vary, while the corrugated collimator retains the hole direction very well but its hole shape may vary. In the case of a PHC, it may have tens of thousands of small hexagonal collimator channels, all pointing in the general direction normal to the surface and parallel to each other. Manufacturing techniques are generally not able to produce a collimator with an individual tolerance for each hole. For large field of view (FOV) collimators (as used in SPECT systems) with tens of thousands of channels, there is typically no cost-effective, accurate and precise method to assess the quality of each hole and determine whether it meets the design criteria.

SUMMARY

Described herein is a framework for characterization of a collimator. In accordance with one aspect, first and second sides of the collimator are photographed to generate first and second image data. An optical characterization map (OCM) may be generated based on the first and second image data, wherein the optical characterization map characterizes the individual channels of the collimator. Quality assessment or image reconstruction may then be performed based on the OCM.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings.

DETAILED DESCRIPTION

In the following description, numerous specific details are set forth such as examples of specific components, devices, methods, etc., in order to provide a thorough understanding of implementations of the present framework. It will be apparent, however, to one skilled in the art that these specific details need not be employed to practice implementations of the present framework. In other instances, well-known materials or methods have not been described in detail in order to avoid unnecessarily obscuring implementations of the present framework. While the present framework is susceptible to various modifications and alternative forms, specific embodiments thereof are shown by way of example in the drawings and will herein be described in detail. It should be understood, however, that there is no intent to limit the invention to the particular forms disclosed; on the contrary, the intention is to cover all modifications, equivalents, and alternatives falling within the spirit and scope of the invention. Furthermore, for ease of understanding, certain method steps are delineated as separate steps; however, these separately delineated steps should not be construed as necessarily order dependent in their performance.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present framework are not described with reference to any particular programming language. It will be appreciated that a variety of programming languages may be used.

The term "image" refers to multi-dimensional data composed of discrete image elements (e.g., pixels for 2D images and voxels for 3D images). The image may be, for example, a medical image of a subject collected by computer tomography, single photon emission computed tomography (SPECT), magnetic resonance imaging, ultrasound, or any other medical imaging system known to one skilled in the art. The image may also be provided from non-medical contexts, such as, for example, remote sensing systems, electron microscopy, etc. Although an image can be thought of as a function from $R^3$ to R, or a mapping to $R^3$, the present methods are not limited to such images, and can be applied to images of any dimension, e.g., a 2D picture or a 3D volume. For a 2- or 3-dimensional image, the domain of the image is typically a 2- or 3-dimensional rectangular array, wherein each pixel or voxel can be addressed with reference to a set of 2 or 3 mutually orthogonal axes.

The terms "pixels" for picture elements, conventionally used with respect to 2D imaging and image display, and "voxels" for volume image elements, often used with respect to 3D imaging, can be used interchangeably. "Pixel" can also refer to an object in data space. It should be noted that the 3D volume image is itself synthesized from image data obtained as pixels on a 2D sensor array and displayed as a 2D image from some angle of view. Thus, 2D image processing and image analysis techniques can be applied to the 3D volume image data. In the description that follows, techniques described as operating upon pixels may alternately be described as operating upon the 3D voxel data that is stored and represented in the form of 2D pixel data for display. In the same way, techniques that operate upon voxel data can also be described as operating upon pixels. In the following description, the variable x is used to indicate a subject image element at a particular spatial location or, alternately considered, a subject pixel. The terms "subject pixel" or "subject voxel" are used to indicate a particular image element as it is operated upon using techniques described herein.

Collimators are typically assessed by averaging regions of collimator channels (or holes). One method is to use the entire large FOV, and to assess, for example, the uniformity or point spread function (PSF) at different locations on the collimator from different emission points in front of the collimator. A complete PSF measurement results in a complete characterization of the image formation process. Parallel collimator quality can be assessed by analysis of a single PSF covering the entire FOV by a point at large distance. Alternatively, scanning of parallel line sources at known locations and in two orthogonal directions has been used to measure effective hole directions as seen from each imaging pixel of the detector FOV.

The drawbacks of current techniques are that they are integral metrics and not able to simultaneously measure hole-to-hole variations or ascertain details of hole shape, septal dimensions, location and direction of each individual channel, as well as potential septal wall defects. Other techniques involve the use of low resolution optical images, with the inability to adapt to various collimator designs and specifications. Such techniques cannot provide the accuracy and precision below 50 μm to allow, for example, comprehensive measurement of hole direction, hole shape defects and septal defects of low energy high-resolution (LEHR) or ultra-high-resolution (UHR) collimators. Some methods use structured light to produce accuracies below 50 μm, but they are not cost effective for larger objects that are several thousands of square centimeters (i.e., LFOV collimators), and many images have to be assembled together. Furthermore, manufacturing of collimators may not produce an absolutely flat surface and the structured light approach can suffer from misidentification of holes in a plane.

Other approaches using mechanical probes or a coordinate-measuring machine (CMM) can only sample very few holes and reach the limit of the probe size itself, as the hole size and shape can be well below 1000 μm. For complicated channel directions, a-priori knowledge of the hole direction is needed, since the probe has to drive into the channel along the principal axis perpendicular to the cross-section of the channel. This may not be possible as the actual angle is the quantity to be measured and is therefore not available.

The present framework provides efficient procedures and systems to comprehensively characterize a collimator for emission imaging. The framework may generate an optical characterization map (OCM) based on the first and second image data of a collimator, and obtain, from the OCM, collimator characteristics, such as channel location, direction, septal thicknesses and septal lengths over a large field of view. The OCM contains the data required for accurate simulation of the collimator (e.g., to build the digital twin of the collimator). The entire process may occur using simulated data to predict image quality based on OCM measurements or simulated OCMs to predict collimator performance.

The framework may be used to comprehensively assess both the quality of the collimator as well the imaging performance of the collimator. The comprehensive characterization may be used for quality control of manufacturing, to predict imaging performance of the collimator, account for detailed individual collimator characteristics of the collimator in the reconstruction of data acquired with the collimator, thereby creating a consistent approach from manufacturing to imaging, increasing yield and improving image quality.

Previous work typically obtains only directions of channels of multichannel collimators, and performs quality control mainly in testing with emission sources. With the higher resolution optical imaging techniques and methods presented herein, relevant features of image quality may be extracted for quality control and image reconstruction without need for emission data from a radiation source. Obtaining emission data is time-consuming, and thus prohibitive for comprehensive testing. Additionally, the framework is advantageously applicable to a wide variety of collimators, such as, but not limited to, parallel-hole, focusing, multi-focusing, multiplexed, non-multiplexed, encoded and time-encoded collimators with respective apertures. The field-of-view dimensions of such collimators may span from few square centimeters to thousands of square centimeters. The framework is also useful during the manufacturing process of, for example, foil collimators produced by stacking half-hex foils in a robotic press. Small initial sections may be quickly evaluated to detect and correct errors in the alignment and tolerances of the press and stacking process.

The present framework also advantageously enables the use of digital cameras and optical lenses with resolutions below 100 μm for small and large FOV measurements alike (>100 MP). Since the collimator is typically large with small channels, sub-millimeter septa thickness and a large number of channels, precision and accuracy over a wide FOV are usually required. Typically, this results in data in the order of gigabytes, which needs storage and processing power that was previously not cost-effective or available. The present framework performs quickly (e.g., within minutes, including processing) and cost effectively, with small non-recurring engineering (NRE) and operational cost per collimator. Additionally, the present framework does not expose users to risks of radiation emission, thereby making it safer to use. These and other features and advantages will be described in more details herein.

Figure 1:
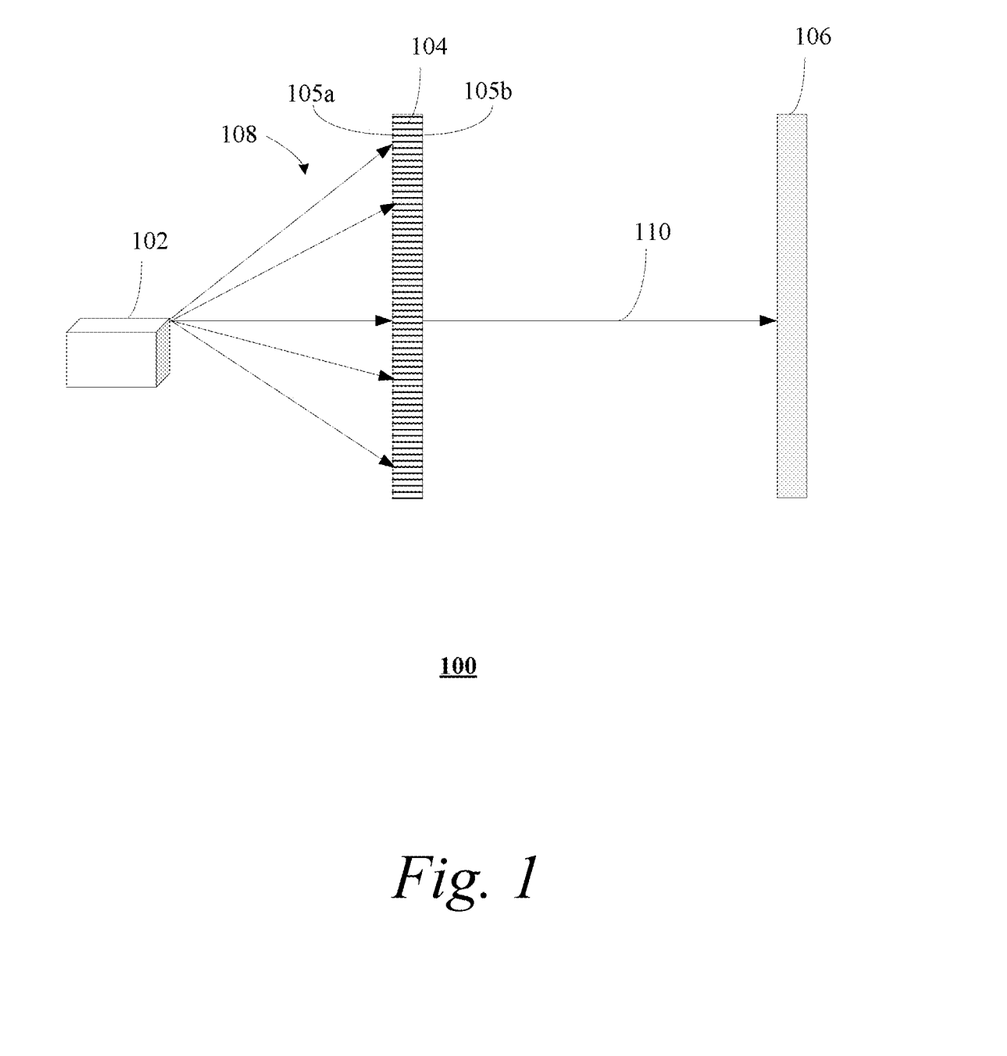
FIG. 1 shows a schematic diagram of an exemplary nuclear medicine imaging system.

FIG. 1 shows a schematic diagram of an exemplary nuclear medicine imaging system 100. The nuclear medicine imaging system 100 includes a detector (e.g., scintillation crystal) 106 and a removable multichannel collimator 104. The collimator 104 is positioned such that it is between the gamma ray source in the object of interest 102 (e.g., patient) and the detector 106 during the operation of the nuclear medicine imaging system 100. The collimator 104 has channels that extend through the thickness of the collimator 104 from a first side 105a to a second side 105b. The collimator 104 collimates the gamma radiation 108 before the radiation 108 reaches the detector 106. An ideal collimator 104 blocks all off-axis rays, so that only on-axis radiation beams 110 reach the detector surface. The on-axis radiation beams 110 propagate in the direction intended by the collimator channels, which in this example are perpendicular to the surface of the collimator 104 and are parallel. Although a parallel-channel, non-focusing collimator 104 is shown, it should be appreciated that the present framework is applicable to other types of collimators, such as astigmatic collimators and focusing collimators (e.g., fan-beam, variable focal length fan beam, cone beam, slant hole, diverging, converging, or coded aperture collimators). The techniques may also be employed to evaluate the design of collimator design/manufacture element (e.g., etch plates for cast collimators) utilized in the manufacture of collimators.

Figure 2:
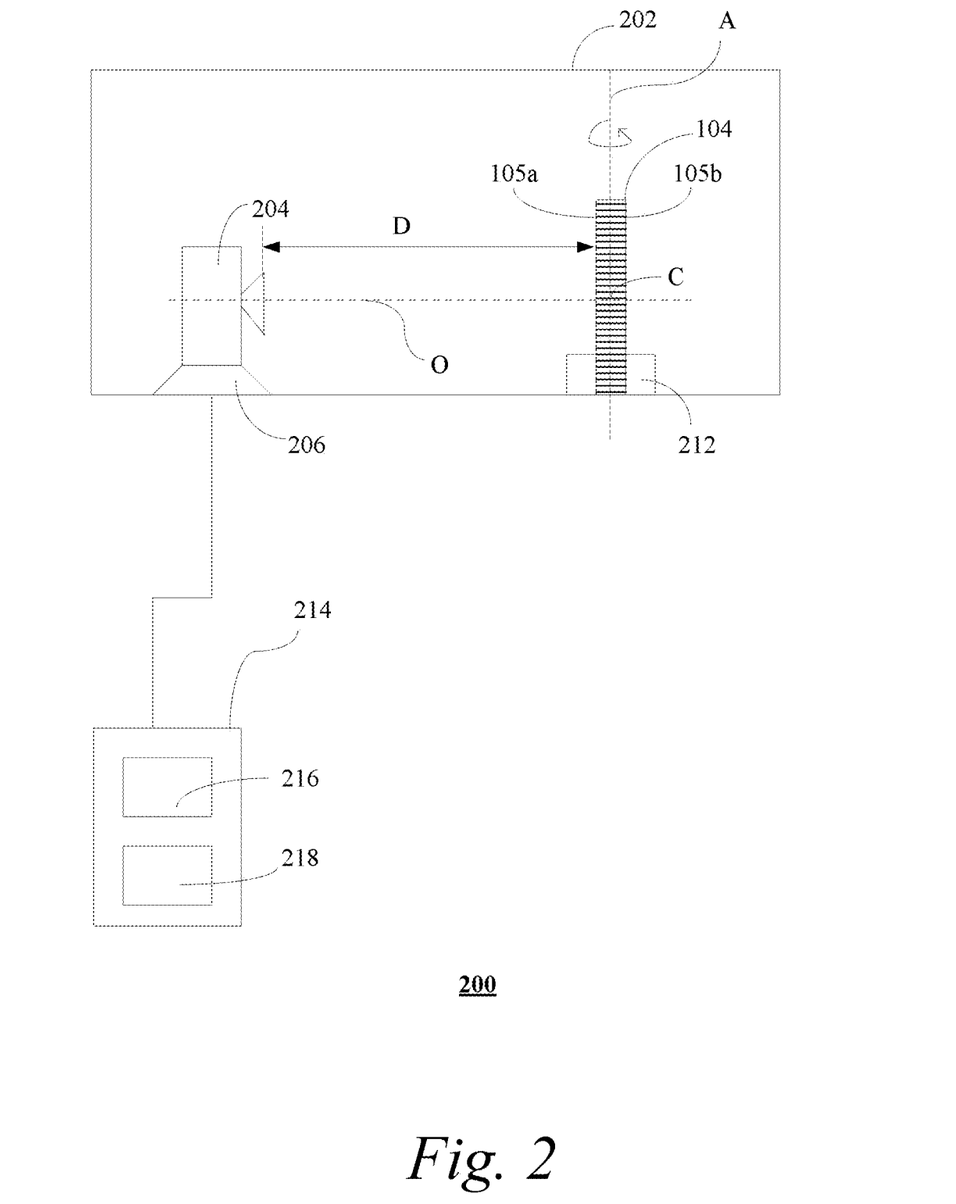
FIG. 2 shows an exemplary system for generating an optical characterization map (OCM) of a collimator.

FIG. 2 shows an exemplary system 200 for generating an optical characterization map (OCM) of a collimator 104. In some implementations, the system 200 includes a high resolution digital camera 204 mounted on a camera mount 206 and a rotatable fixture 212 for holding the collimator 104. The digital camera 204 is generally an electronic imager that uses an image sensor (e.g., charge-coupled device (CCD) or Complementary Metal Oxide Semiconductor (CMOS) chip) to convert light into electrical signals. The camera 204 is chosen to provide images with high spatial resolution below at least 100 μm (e.g., 25 μm to 50 μm), adequate for the determination of individual detailed characteristics of each channel of the collimator 104. Exemplary characteristics include, but are not limited to, channel location (e.g., center of hole), channel spacing, septal thickness and distortion of hole shape. It may also be desirable that the field-of-view of the camera 204 be large enough to capture each surface (105a, 105b) of the collimator with a single exposure.

The system 200 may include a computer system 214 communicatively coupled to the digital camera 204. The computer system 214 is configured with a processor 216 (e.g., graphics processing unit or GPU) suitable for performing image processing necessary to process the digital image data generated by the camera 204. The processor 216 is communicatively coupled to a non-transitory computer-readable media 218 suitable for storing the digital image data and computer-readable program code. The non-transitory computer-readable media 218 can be one or more of data storage devices commonly used in computers. Computer system 214 may further include one or more display devices (e.g., monitor), one or more input devices (e.g., mouse or keyboard), support circuits such as a cache, a power supply, clock circuits and a communications bus. Various other peripheral devices, such as additional data storage devices and printing devices, may also be connected to the computer system 214.

The present technology may be implemented in various forms of hardware, software, firmware, special purpose processors, or a combination thereof, either as part of the microinstruction code or as part of an application program or software product, or a combination thereof, which is executed via the operating system. In some implementations, the techniques described herein are implemented as computer-readable program code tangibly embodied in non-transitory computer-readable media 218.

The fixture 212 holds the collimator 104 in vertical orientation and the camera mount 206 is provided at a fixed position relative to the fixture 212 such that the camera 204 is at a fixed distance D from the surface of the collimator 104 mounted in the fixture 212. Optionally, the collimator 104 and the camera 204 are contained in a light box 202 that limits the amount of ambient light falling on the collimator. To minimize misidentification due to shadowing, one or more colored light sources may be used to illuminate the collimator 104. The one or more colored light sources may be used to backlight holes of the collimator 104, so that the walls of a tilted hole, but not the surface around the hole, are illuminated in a different color to yield a better definition of the hole at the collimator surface.

The collimator 104 has two sides 105a and 105b. The fixture 212 is rotatable about its vertical axis A so that each of the two sides 105a, 105b of the collimator 104 can be presented to the camera 204 for acquiring digital images of the two sides. The vertical axis A will also be referred to herein as the axis of rotation A. The fixture 212 is configured to hold the collimator 104 in vertical orientation and have the vertical axis A of the fixture extending through the center of the thickness of the collimator 104. This configuration allows the two sides 105a, 105b of the collimator 104 to be parallel to the vertical axis A of the fixture 212 and therefore maintains the distance D from the camera 204 when each of the two sides 105a, 105b are facing the camera 204. Ideally, the optical axis O of the camera is exactly perpendicular to the vertical axis A of the fixture 212. This ensures that the optical axis of the camera is perpendicular to the surfaces of the two sides 105a, 105b of the collimator when facing the camera 204. Ideally, the optical axis of the camera 204 intersects the collimator surface at the mechanical center C of the collimator 104 so that the collimator is centered in the camera's field-of-view. When a given side of the collimator 104 is facing the camera 204, the spatial relationship between the camera 204 and the collimator 104 is characterized by the configuration described above. Ideally, the configuration of the camera 204 and the collimator 104 ensures there is no component of geometric distortion in the digital images of the two sides 105a, 105b acquired by the camera 204 attributable to non-ideal alignment of the camera with respect to the surface of the collimator 104.

Figure 3:
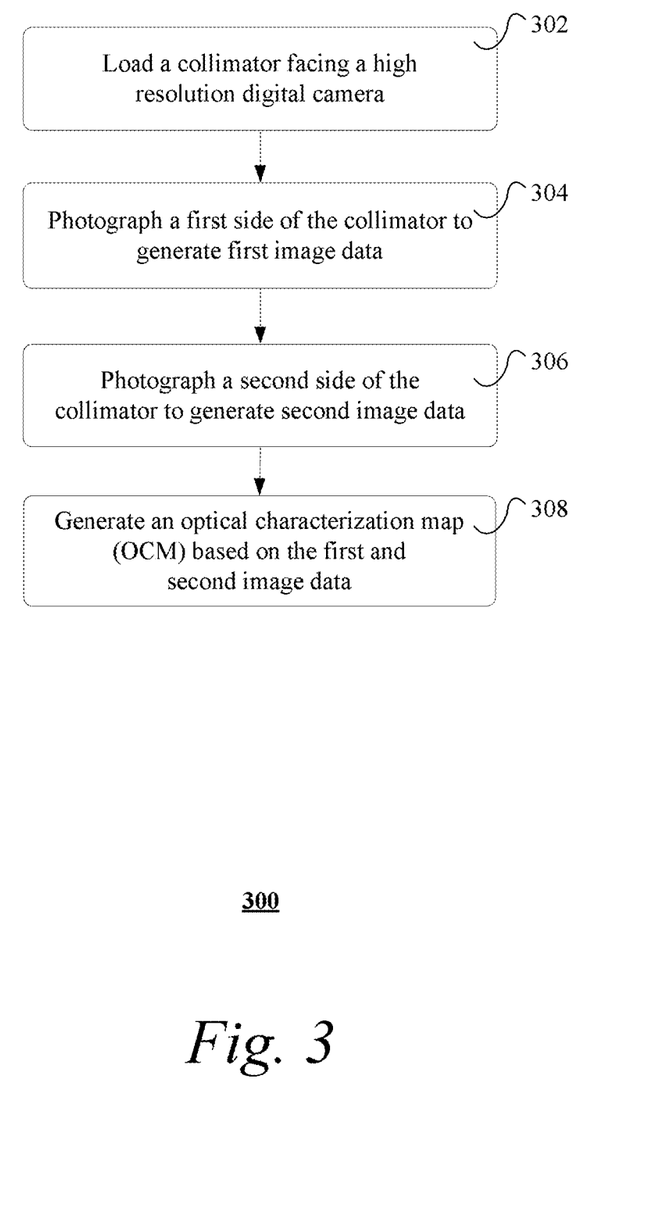
FIG. 3 shows an exemplary method of generating an optical OCM of a collimator by a computer system.

FIG. 3 shows an exemplary method 300 of generating an optical characterization map (OCM) of a collimator by a computer system. It should be understood that the steps of the method 300 may be performed in the order shown or a different order. Additional, different, or fewer steps may also be provided. Further, the method 300 may be implemented with the system 200 of FIG. 2, a different system, or a combination thereof.

At 302, a collimator 104 is loaded into the fixture 212 facing a high resolution digital camera 204 (as shown in FIG. 2). The collimator 104 is oriented with one of the two sides 105a, 105b of the collimator 104 facing the camera 204 for acquiring a digital image of that side. The collimator may be large (e.g., >1000 square centimeters, or 2000 square centimeters) with small channels (e.g., in the order of millimeters), sub-millimeter septa thickness and a large number of channels (e.g., >10,000, typically 40,000-60,000).

At 304, the camera 204 is used to photograph a digital image of the first side 105a of the collimator 104. The term "photograph" generally refers to taking or acquiring a digital image (or digital image data) of a subject using the digital camera 204. The resulting digital image may be stored in the non-transitory computer readable media 218 as a first image data.

At 306, a second side 105b of the collimator 104 is photographed. In some implementations, the same camera 204 is used to photograph the second side 105b. The fixture 212 is rotated about its axis of rotation A 180 degrees so that the second side 105b of the collimator 104 is now facing the camera 204 for photographing. During the rotation of the collimator 104, the camera 204 is immobile so that the camera's position remains fixed relative to the fixture 212. Alternatively, instead of rotating the collimator 104, the second side 105b of the collimator 104 may be photographed using a second digital camera. The second camera may be mounted at a fixed distance from the fixture 212. The two cameras may be positioned facing each other with the fixture 212 positioned in the middle. Since images of the two sides of the collimator 104 can be taken without rotating the collimator 104, this would eliminate the need for correcting the rotational error of the fixture 212. The resulting digital image of the second side 105b is stored in the non-transitory computer readable media 218 as a second image data.

At 308, the processor 216 generates an optical characterization map (OCM) based on the first and second image data. The OCM characterizes the individual channels of the collimator 104. The OCM contains the data required for accurate simulation of the collimator (e.g., to build the digital twin of the collimator). Once the position of the septa is known, imaging processing methods may be performed on the first and second image data to generate first and second optical maps. For example, image segmentation and boundary detection may be performed to identify pixels belonging to the first and second channel openings for the respective first side 105a and the second side 105b of the collimator 104. The center locations of channel openings may be derived based on the first and second optical maps. The term "channel opening" as used herein refers to the hole formed on the surface of the collimator 104 by the intersection of a given channel and the surface of the collimator 104. Thus, for any given channel, there are two channel openings, one on the first side 105a and another on the second side 105b of the collimator 104. The first and second optical maps may each be stored in, for example, two-dimensional arrays.

The OCM may then be generated by registering the first and second optical maps and identifying the pixels belonging to each channel opening of the collimator based on the registered first and second optical maps. In some implementations, the OCM is represented by a list of tuples. An exemplary tuple is as follows: [channel_number, first_or_second], wherein channel_number represents the unique identifier of a channel, first_or_second specifies whether a pixel belongs to the first or second optical map (or image data). Additionally, or alternatively, the OCM may include direction vectors, wherein each direction vector represents the pointing direction (or orientation) vector of a channel of the collimator at a particular location. Other methods of representing the OCM, such as including a measure of the septal thickness or local sensitivity at each channel, are also possible.

Figure 4:
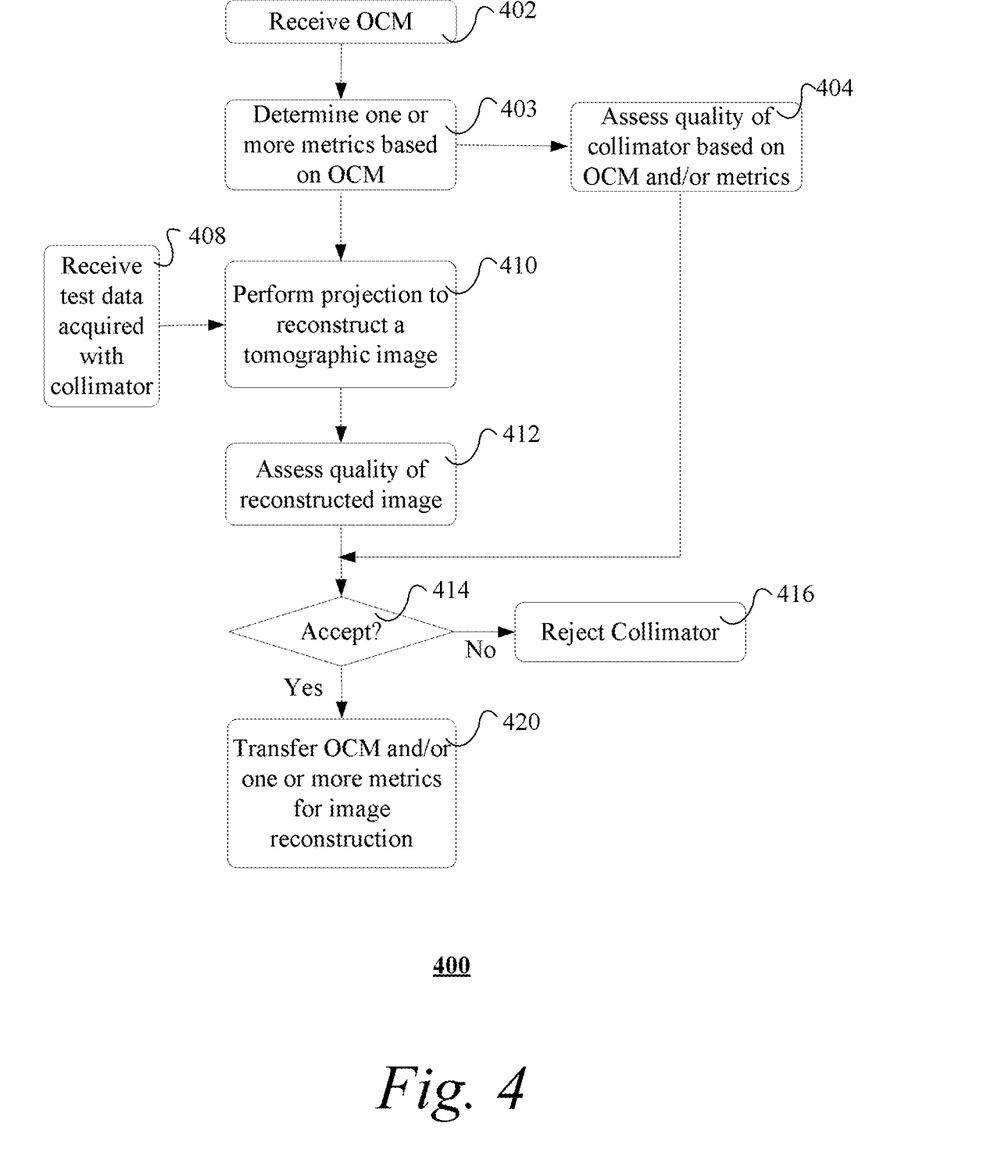
FIG. 4 shows an exemplary method of quality assessment using the OCM.

FIG. 4 shows an exemplary method 400 of quality assessment using the OCM. It should be understood that the steps of the method 400 may be performed in the order shown or a different order. Additional, different, or fewer steps may also be provided. Further, the method 400 may be implemented with the system 200 of FIG. 2, a different system, or a combination thereof.

At 402, the processor 216 receives an OCM of a collimator 104. The OCM may be retrieved from, for example, a non-transitory computer-readable media 218.

At 403, the processor 216 determines one or more metrics based on the OCM. The one or more metrics represent detailed characteristics of each individual channel of the collimator. The metrics may be used for image reconstruction and/or quality assessment. In some implementations, the metrics include, but are not limited to, an optical vector map (OVM), an optical sensitivity map (OSM), and an optical shape deformation map (OSDM). It should be appreciated that other types of metrics may also be derived from the OCM.

The optical vector map (OVM) may be a two-dimensional array, wherein each value represents the pointing direction (or orientation) vector of a channel of the collimator at a particular location. The OVM may be obtained by comparing the positions of the two channel openings associated with a given channel in the OCM relative to one another. More particularly, each entry in the OVM may include a pointing direction vector of a given channel, which is determined by calculating the line segment (or vector) from a center location of a first channel opening to the corresponding center location of second channel opening. Other metrics may be calculated based on the OVM. For example, septal penetration may be calculated via Monte Carlo simulation of the collimator using OVM characterization.

The optical sensitivity map (OSM) may be a two-dimensional array, wherein each value represents the sensitivity (solid angle and/or utility factor) of a channel of the collimator at a particular location. "Sensitivity" generally refers to the percentage of incident photons that pass through the collimator. Sensitivity of each channel may be determined based on channel hole area, bore length and channel spacings derived from the OCM.

Figure 5:
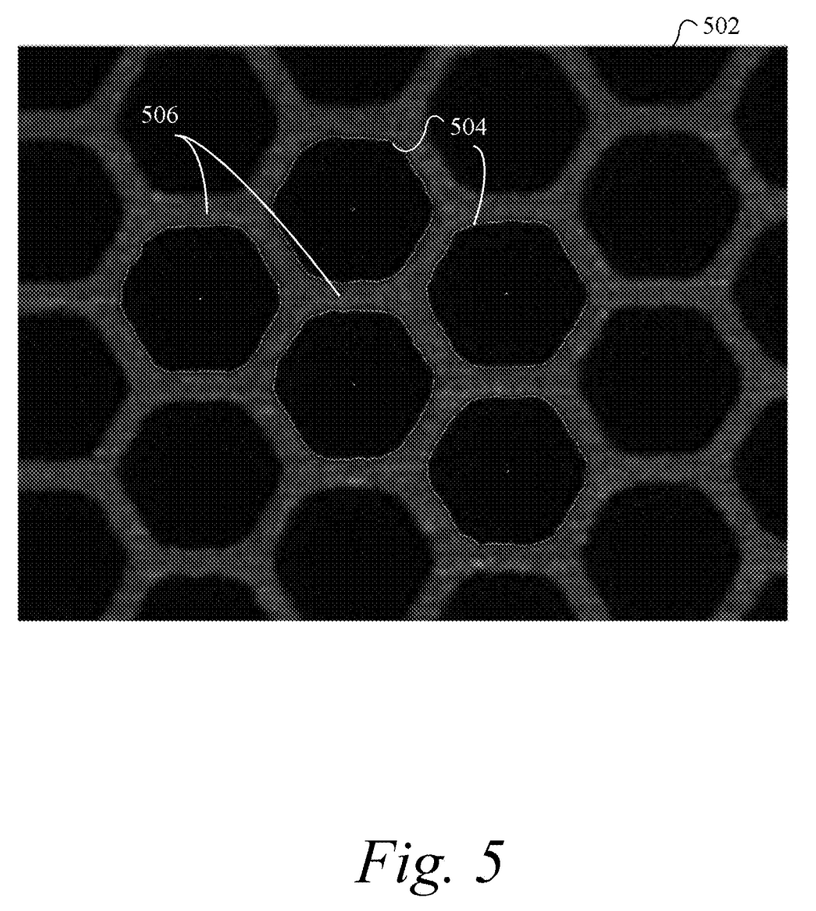
FIG. 5 shows an image of an exemplary collimator segment with channel characterization.

FIG. 5 shows an image 502 of an exemplary collimator segment with channel characterization. The collimator is a cast hexagonal-hole collimator. The collimator image 502 illustrates the characterization of casted holes 504 that enables the computation of spacing between tunnels, tunnel locations and thickness of the septa 506 that can be achieved with a digital camera with a high resolution of 27μ. The characterization shows that the six sides of the channels 504 are of unequal thickness. Distorted shapes also produce distorted point spread response functions (PSRFs).

The optical shape deformation map (OSDM) may be a two-dimensional array, wherein each value represents the hole shape deformation of a channel of the collimator at a particular location. The hole shape deformation describes the distortion of the hole shape. The hole shape deformation may be characterized by, for example, the length and relative angle of each septa for a unit cell, or the shifts (or offset) between bottom and top half hex holes, in the case of stacked corrugated foils. Using a small initial segment of a full collimator, the OSDM may be used to evaluate the quality of the stacking process and initiate adjustment of the press and stacking processes.

Figure 6:
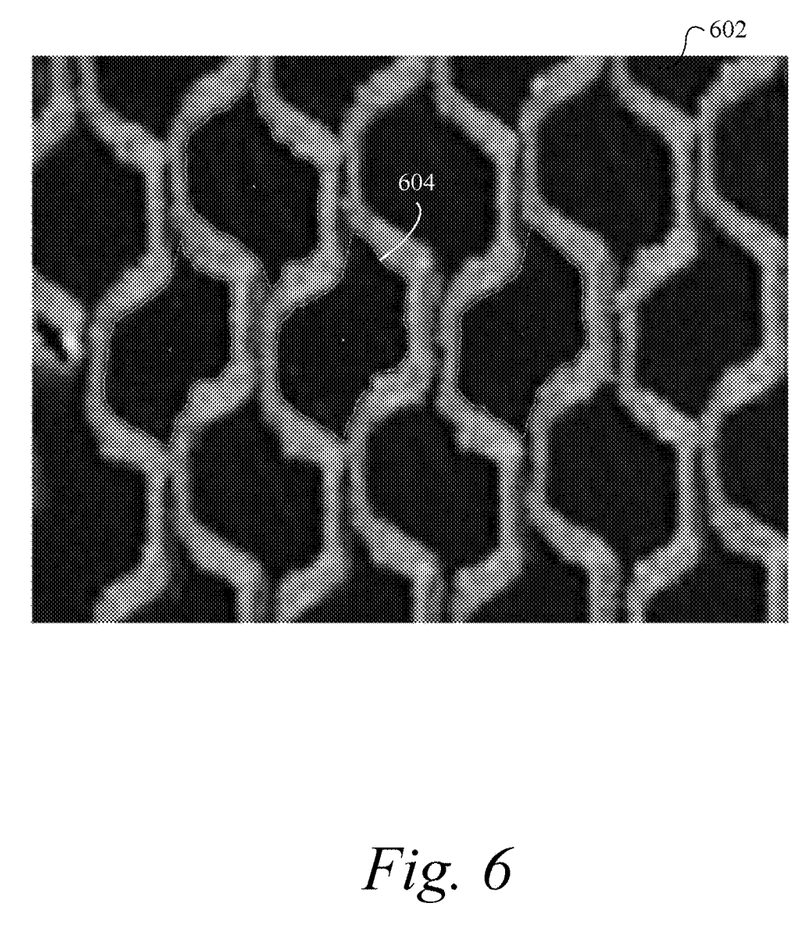
FIG. 6 shows an image of an exemplary collimator segment with hole shape distortions.

FIG. 6 shows an image 602 of an exemplary collimator segment with hole shape distortions. The collimator is a stacked foil collimator with distorted hole shapes 604. The hole shape is sensitive to alignment of foil strips during the stacking process. Misalignment of the foil strips that form the channels in stacked foil collimators causes substantial areas of the channel wall to have lower thickness, thereby increasing septa penetration. Evaluation of such a segment image 602 during the manufacturing process is useful for adjusting the collimator production press, thereby obviating the cost of generating multiple scrap collimators.

Returning to FIG. 4, at 404, the quality of the collimator 104 is assessed based on the OCM and/or one or more metrics. This may be performed by, for example, a human expert or a numerical observer (e.g., artificial intelligence or a statistical evaluation of errors of hole directions from those expected from design). In some implementations, quality assessment is performed by comparing the parameters (e.g., locations of the channel openings) extracted from the OCM and/or one or more metrics with the expected parameters according to the collimator design. The expected parameters may be derived from, for example, a computer-aided design (CAD) file containing the collimator design.

Figure 7:
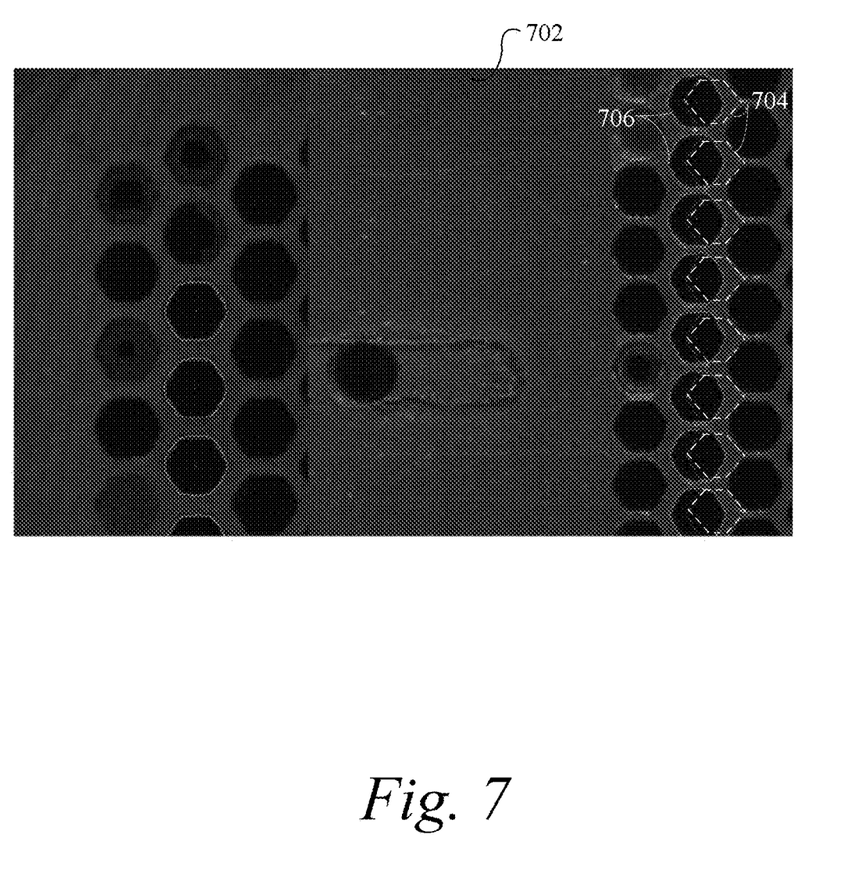
FIG. 7 shows an image of an exemplary collimator segment with channels that are not located in locations expected according to design parameters.

FIG. 7 shows an image 702 of an exemplary collimator segment with channels that are not located in locations expected according to design parameters. The collimator image 702 represents the results of comparing the actual detected channel opening locations on the collimator and the expected channel opening locations. The broken lines 704 represent the expected locations of the channel openings per design. The solid lines 706 represent the estimated boundaries of the actual detected channel openings.

One possible quality assessment criterion may be, for example, determining whether there is sufficient spacing (or septa width) between channel openings of the collimator. For example, if there is sufficient spacing between the channel openings for more than a predetermined fraction of the channel openings, the collimator 104 is determined to have passed the quality assessment. Otherwise, the collimator 104 is determined to have failed the quality assessment. Another possible quality assessment criterion may be determining whether the channels of the collimator point along respective design directions (e.g., substantially same directions for parallel-channel collimator). For example, if more than a predetermined fraction of the channels point along respective design directions, the collimator 104 may be determined to have passed the quality assessment. Other types of quality assessment criteria based on other types of parameters stored in metrics derived from the OCM (e.g., sensitivity, septal penetration, hole deformation) may also be applied.

Returning to FIG. 4, at 408, the processor 216 receives test data acquired with the collimator 104. As used herein, the term "acquired" refers to either simulated or measured. In some implementations, test data is measured using simplified objects (or phantoms) that contain radioactivity to confirm the quality of the collimator. Alternatively, test data may be simulated by producing projections using simulated gamma ray emissions and detection equipment as intended for use with a digital twin of the collimator. The term "digital twin" refers to a digital characterization of a physical object that comprehensively and uniquely describes the individual physical object. Gamma ray emissions may be simulated using, for example, ray tracing and Monte Carlo simulation methods to model the randomness of gamma rays.

At 410, the processor 216 performs forward/back projections based on the OCM to reconstruct a tomographic image of a sample object (e.g., heart). The OCM may be used to provide (or extract) the channel direction vectors of the collimator 104, which are used to determine the directions of the projections.

At 412, quality of the reconstructed image is assessed. The reconstructed image may be inspected for, for example, visual artifacts that may be introduced by the collimator 104. For example, a cardiac acquisition may be simulated to reconstruct a simulated image of the heart. The reconstructed image may then be compared to the model used for simulation or, for actual test data, to the phantom geometry in order to identify any artifacts that may have been introduced by the collimator 104. Such assessment may be visually performed by a human expert or automatically performed by a numerical observer (e.g., artificial intelligence modules trained to perform the assessment).

At 414, a determination of whether the collimator 104 may be rejected or accepted for the intended use is made. If both the quality of the collimator 104 and the quality of the reconstructed image are determined to fail, the collimator 104 is rejected at 416. The OCM and/or one or more metrics may be used to adjust the collimator production system. For example, the stacking alignment of the robotic press may be adjusted (or tweaked) to reduce hole shape deformation and/or septa penetration. Other parameters may also be adjusted for other processes of the collimator manufacturing (e.g., casting process). Accordingly, optical measurements may be quickly performed on a sample cast collimator or small sample stack of a foil collimator to facilitate adjustments so as to optimize the system and ensure that no more than one "bad" collimator is produced before correction. If either the quality of the collimator 104 or the quality of the reconstructed image is determined to pass the assessment, then the method proceeds to 420.

At 420, the OCM and/or the one or more metrics of the specified collimator 104 are transferred to an imaging system for use in image reconstruction of emission image data acquired using the collimator 104. In some implementations, emission image data of an object of interest is acquired using a nuclear imaging system (e.g., SPECT), such as the nuclear medicine imaging system 100 as described previously with respect to FIG. 1. Other types of imaging modalities or systems may also be used.

Image reconstruction may be performed based on pointing direction vectors of the channels, such as those stored in the OVM and/or OCM. The channel direction vectors may be utilized to determine the directions of the forward-projections and/or back-projections during tomographic reconstruction of the emission image data.

While the present framework has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

What is claimed is:

1. A method of characterizing a large field-of-view collimator, comprising:
   providing at least one digital camera mounted at a fixed distance from the collimator, wherein the at least one digital camera and the collimator are contained in a light box;
   photographing, using the at least one digital camera, a first side of the collimator to generate a first image data;
   photographing, using the at least one digital camera, a second side of the collimator to generate a second image data;
   generating an optical characterization map (OCM) based on the first and second image data, including generating first and second optical maps based on the first and second image data using one or more image processing techniques and identifying pixels belonging to individual channels of the collimator based on the first and second optical maps, wherein the optical characterization map stores at least measurements of the individual channels of the collimator based on the first and second optical maps; and
   performing quality assessment based on the OCM, including determining sensitivities of the individual channels using the measurements stored in the OCM.

2. The method of claim 1 wherein photographing the first side of the collimator and photographing the second side of the collimator comprises photographing the first and second sides of the collimator at a high spatial resolution below at least 100 μm.

3. The method of claim 1 wherein providing the at least one digital camera comprises positioning first and second digital cameras facing each other with the collimator positioned between the first and second digital cameras, wherein the first and second digital cameras photograph the first and second sides of the collimator respectively.

4. The method of claim 1 wherein photographing the second side of the collimator to generate the second image data comprises rotating the collimator 180 degrees so that the second side faces the at least one digital camera.

5. The method of claim 1 wherein the one or more image processing techniques comprise image segmentation and boundary detection.

6. The method of claim 1 wherein performing the quality assessment based on the OCM comprises:
   determining one or more metrics based on the OCM; and
   performing the quality assessment using the one or more metrics.

7. The method of claim 6 wherein determining the one or more metrics comprises determining an optical vector map (OVM).

8. The method of claim 6 wherein determining the one or more metrics comprises determining an optical sensitivity map (OSM), wherein values of the OSM represent the sensitivities at particular locations, wherein the sensitivities are indicative of amount of incident photons that pass through the collimator and are determined based at least in part on channel hole area, bore length, channel spacing or a combination thereof derived from the OCM.

9. The method of claim 6 wherein determining the one or more metrics comprises determining an optical shape deformation map (OSDM).

10. The method of claim 1 wherein performing the quality assessment based on the OCM comprises comparing parameters extracted from the OCM or one or more metrics derived based on the OCM with expected parameters according to a collimator design.

11. The method of claim 1 wherein performing the quality assessment based on the OCM comprises determining whether there is sufficient spacing between channel openings of the collimator.

12. The method of claim 1 wherein performing the quality assessment based on the OCM comprises determining whether individual channels of the collimator point along respective design directions.

13. The method of claim 1 wherein performing the quality assessment based on the OCM comprises:
   performing a projection based on the OCM to reconstruct an image of a sample object; and
   assessing quality of the reconstructed image.

14. A system for characterizing a collimator, comprising:
   at least one digital camera mounted at a fixed distance from the collimator, wherein the at least one digital camera photographs first and second sides of the collimator to generate respective first and second image data, wherein the at least one digital camera and the collimator are contained in a light box; and
   a computer system communicatively coupled to the at least one digital camera, the computer system including a non-transitory memory device for storing computer readable program code, and a processor device in communication with the memory device, the processor device being operative with the computer readable program code to perform steps including
      receiving the first and second image data,
      generating an optical characterization map (OCM) based on the first and second image data, including generating first and second optical maps based on the first and second image data using one or more image processing techniques and identifying pixels belonging to individual channels of the collimator based on the first and second optical maps, wherein the OCM stores measurements of the individual channels of the collimator based on the first and second optical maps, and
      performing quality assessment based on the OCM, including determining sensitivities of the individual channels using the measurements stored in the OCM.

15. The system of claim 14 wherein the at least one digital camera is a high resolution camera capable of photographing the first and second image data at a high spatial resolution below at least 100 μm.

16. The system of claim 14 wherein the at least one digital camera comprises first and second digital cameras positioned facing each other with the collimator positioned between the first and second digital cameras, wherein the first and second digital cameras photograph the first and second sides of the collimator respectively.

17. The system of claim 14 wherein the collimator comprises a parallel-channel collimator, a fan-beam collimator, a variable focal length fan beam collimator, a cone beam collimator, a slant hole collimator, a diverging collimator, a converging collimator or a coded aperture collimator.

18. The system of claim 14, wherein the one or more image processing techniques comprise image segmentation and boundary detection.

19. The system of claim 14, wherein the processor device is operative with the computer readable program code to perform the quality assessment by comparing parameters extracted from the OCM or one or more metrics derived based on the OCM with expected parameters according to a collimator design.

20. One or more non-transitory computer readable media embodying a program of instructions executable by a machine to perform operations, the operations comprising:

receiving, from at least one digital camera, first and second image data of respective first and second sides of a collimator, wherein the first and second image data has a high spatial resolution of below at least 100 µm, wherein the at least one digital camera and the collimator are contained in a light box;

generating an optical characterization map (OCM) based on the first and second image data, including generating first and second optical maps based on the first and second image data using one or more image processing techniques and identifying pixels belonging to individual channels of the collimator based on the first and second optical maps, wherein the OCM stores measurements of the individual channels of the collimator based on the first and second optical maps;

performing quality assessment based on the OCM, including determining sensitivities of the individual channels using the measurements stored in the OCM; and transferring the OCM to an imaging system for performing image reconstruction.

* * * * *